United States Patent
Zatz et al.

(10) Patent No.: US 6,821,508 B2
(45) Date of Patent: Nov. 23, 2004

(54) COMPOSITION AND METHOD FOR TOPICAL NAIL TREATMENT

(75) Inventors: Joel L. Zatz, Metuchen, NJ (US); Gouri G. Malhotra, New York, NY (US)

(73) Assignee: Rutgers, the State University, New Brunswick, NJ (US)

( * ) Notice: Subject to any disclaimer, the term of this patent is extended or adjusted under 35 U.S.C. 154(b) by 211 days.

(21) Appl. No.: 10/185,518

(22) Filed: Jun. 27, 2002

(65) Prior Publication Data

US 2003/0091519 A1 May 15, 2003

Related U.S. Application Data

(60) Provisional application No. 60/300,828, filed on Jun. 27, 2001.

(51) Int. Cl.$^7$ ............................. A61K 7/04; A61K 7/00; A61K 31/20; A01N 25/34
(52) U.S. Cl. ......................... 424/61; 424/401; 424/404; 514/553; 514/558
(58) Field of Search ........................ 424/61, 404, 401; 514/553, 558

(56) References Cited

U.S. PATENT DOCUMENTS 5,472,698 A * 12/1995 Rawlings et al. ........... 424/401
5,696,164 A 12/1997 Sun et al. .................... 514/526
6,123,930 A 9/2000 Agnus et al. ................. 424/61

FOREIGN PATENT DOCUMENTS

EP 0 440 298 A1 1/1991
EP 0 503 988 B1 3/2000

OTHER PUBLICATIONS

Malhotra et al., "Characterization of the physical factors affecting nail permeation using water as a probe", J. Cosmet. Sci. 2000 51:367–377.

Mertin et al., "In–vitro Permeability of the Human Nail and of a Keratin Membrane from Bovine Hooves: Influence of the Partition Coefficient Octanol/Water and the Water Solubility of Drugs on their Permeability and Maximum Flux", J. Pharm. Pharmacol. 1997 49:30–34.

Walters et al., "Physiocochemical Characterization of the Human Nail: I. Pressure Sealed Apparatus for Measuring Nail Plate Permeabilities", The Journal of Investigative Dermatology 1981 76:76–79.

* cited by examiner

*Primary Examiner*—Shelley A. Dodson
(74) *Attorney, Agent, or Firm*—Licata & Tyrrell P.C.

(57) ABSTRACT

The invention discloses a composition comprising a sulfur-containing glycine residue combined with urea to increase the permeation of an active agent or drug through human nail tissue. The invention further provides methods of applying the composition to a nail surface.

3 Claims, No Drawings

COMPOSITION AND METHOD FOR TOPICAL NAIL TREATMENT

INTRODUCTION

This application claims the benefit of priority from U.S. Provisional Application Ser. No. 60/300,828, filed Jun. 27, 2001, incorporated herein by reference.

BACKGROUND OF THE INVENTION

Onychomycosis is a fungal disease of the human nail. The symptoms of this disease are split, thickened, hardened, and rough nail plates. This is caused by any of a number of organisms and is particularly prevalent in the elderly. Typically, fungal infections are treated by topical application of antifungal agents and/or oral administration of antifungal agents. The main challenge associated with developing topical treatments for nail disorders is to deliver the active compounds in therapeutically effective concentrations to the site of infection, which is often under the nail. If the nail barrier is modified, reduced, or eliminated, topical antifungal drug treatment is effective for onychomycosis. For example, both miconazole and ketoconazole have been demonstrated to be effective in topically treating onychomycosis after nail removal. However, most consumers would certainly prefer a less dramatic treatment of nail fungal infection than removal of the nail.

Nail psoriasis is another common nail disorder affecting up to 50% of patients with psoriasis. Characteristic nail psoriasis symptoms include pitting, which appears as punctuated or irregularly shaped depressions arranged on the surface of the body of the nail; discoloration of the nail bed; onycholysis or detachment of the body of the nail from the nail bed; subungual keratosis; or anomalies of the body of the nail. As with nail fungal infections, current methods of treatment are not satisfactory. One treatment method, the systemic method, consists of long-term administration of methotrexate, retinoids or cyclosporin A orally which can lead to intoxication. Another method consists of injecting intralesional corticosteroids. This method is naturally very painful and patients often refuse treatment. A further method consists of surgically removing the affected nails, but intervention is only temporary because within one week after regeneration of the body of the nail psoriasis may return. A fourth, gentler, method consists of treating the nails locally with specific, antipsoriatic substances such as dithranol, vitamin D analogs, or corticosteroids, however, as with nail infections, effective delivery of the active compounds is a problem.

The nail plate is thick, hard, dense, and represents a formidable barrier for drug penetration. Although nail material is similar to the stratum corneum of the skin, being derived from epidermis, it is composed primarily of hard keratin, which is highly disulfide-linked, and is approximately 100-fold thicker than stratum corneum. In order to deliver a sufficient amount of drug into the nail plate, the permeability of the nail plate to the drug must be enhanced. This is particularly true in fungal diseases where a common symptom of the disease is thickened nail plate.

Recent research efforts have focused on improving penetration by chemically modifying the nail keratin matrix (Kobayashi, et al. (1998) *Chem Pharm Bull* 46(11):1797–1802). Examples of compounds which interact with keratin include mercaptan compounds, sulfites and bisulfites, keratolytic agents, and surfactants.

Mercaptan Compounds. The utility of compounds possessing sulfhydryl (SH) groups, i.e., mercaptan compounds, to enhance nail penetration has been reported (Soong (1991) Transport properties of drugs and model compounds across the human nail. Ph.D. Dissertation. University of Minnesota; U.S. Pat. No. 5,696,164). EP0440298 A1 discloses the use of sulfur-containing cysteine derivatives in topical preparations for treatment of nail diseases such as onychomycosis. Furthermore, U.S. Pat. No. 5,696,164 to Sun et al. discloses the use of sulfhydryl-containing cysteine and N-acetyl cysteine in combination with urea to increase drug permeability in a nail plate. Moreover, U.S. Pat. No. 6,123,930 provides a composition of sulphur-bearing amino acid together with sodium tetraborate for the treatment of nails. Mercaptan compounds reduce keratin in human hair via a sequence of two reversible, nucleophilic displacements (Robbins (1997) Chemical and physical behavior of human hair, 3rd ed. New York: Springer-Verlag. pp. 93–130; Wolfram (1981) In: Orfanos, et al, eds. Hair research: Status and future aspects. New York: Springer-Verlag. pp. 479–500). High concentrations of the mercaptan and alkaline pH favor the forward reaction due to the increased formation of the mercaptide anion required for reduction (Herrmann (1963) *Trans Farady Soc* 59:1663–1671; Wickett (1983) *J Soc Cosmet Chem* 34:301–316).

Pyrithione (2-mercaptopyridine-1-oxide, PTO) is a fungicidal and bactericidal agent. The zinc (ZnPTO) and sodium (NaPTO) derivatives of pyrithione possess fungicidal activity and ZnPTO is commonly used in antidandruff preparations. Compounds containing a SH group are themselves oxidized while reducing disulfide linkages in nail keratin (Robbins (1997) Chemical and physical behavior of human hair, 3rd ed. New York: Springer-Verlag. pp. 93–130; Wolfram (1981) In: Orfanos, et al, eds. Hair research: Status and future aspects. New York: Springer-Verlag. pp. 479–500). For PTO, such self-oxidation would result in the formation of the dipyrithione dimer which possesses antifungal activity.

Terpenes are also known to be effective skin penetration enhancers. Menthone, in particular, has been found to enhance penetration of several different drugs across skin (Kragh, et al. (1993) *STP Pharma Sci* 3:499–506; Yamane, et al. (1995) *Int J Pharm* 116:237–251). 1,4-Dithiothreitol, which contains two SH groups, has been shown to be a particularly effective reducing agent, because this molecule can undergo rapid autocleavage during the reduction process to form a sterically favored cyclic disulfide as the end product (Wolfram (1981) In: Orfanos, et al, eds. Hair research: Status and future aspects. New York: Springer-Verlag. pp. 479–500).

Sulfites and Bisulfites. Sulfites and bisulfites are known to be reducers of disulfide linkages in keratin, and thus are popularly used for permanent waving of hair (Robbins (1997) Chemical and physical behavior of human hair, 3rd ed. New York: Springer-Verlag. pp. 93–130).

Keratolytic Agents. Salicylic acid (SA), urea (U), and guanidine hydrochloride (GnHCl) are substances which may disrupt the tertiary structure, and possibly secondary linkages (such as hydrogen bonds) in keratin, thus promoting penetration through the nail. Compounds such as urea and guanidine hydrochloride are known to be denaturing agents, resulting in disruption of the water structure around proteins, decreasing the hydrophobic effect, and thereby promoting unfolding and dissociation of the protein molecules (Alber (1989) In: Fasman G D, ed. Prediction of protein structure and the principles of protein conformation. New York: Plenum Press. pp. 161–192; Manning, et al. (1989) *Pharm Res* 6(11):903–918; Mathews and van Holde (1990) Biochemistry. Redwood City: The Benjamin/Cummings Publishing Co, pp. 213–215).

Surfactants. Surfactants, primarily of the anionic type, are known to be able to interact with keratin. Concentrated solutions of sodium lauryl sulfate are commonly used to solubilize proteins. These detergents are thought to form micelles around individual polypeptide chains and thus promote dissociation of protein molecules (Mathews and van Holde (1990) Biochemistry. Redwood City: The Benjamin/Cummings Publishing Co, pp. 213–215).

European Patent Application EP 503988 discloses other nail penetration agents including glycols, glycol ethers, dimethyl sulfoxide, caprolactam, and other hydrophilic compounds to facilitate the penetration of allylamine fungicides into the nail.

SUMMARY OF THE INVENTION

The present invention provides a composition which comprises sulfur-containing glycine residues and urea to increase the permeation of an active agent through nail tissue.

The invention further provides methods of applying the composition of the invention to a nail prior to, or in conjunction with, an active agent to increase the permeation of said active agent through the nail tissue.

DETAILED DESCRIPTION OF THE INVENTION

The present invention relates to methods and a composition of N-(2-mercaptopropionyl) glycine (MPG) and urea for treating fingernails and toenails. Of many combinations of potential penetration enhancers, the composition of the present invention was the most effective. Results of a screen monitoring tritiated water permeation of gels containing keratolytic agents either alone or in combination with a mercaptan derivative of an amino acid (MPG) are shown in Table 1.

TABLE 1

| Gel | Enhancer | J* (mg cm$^{-1}$h$^{-1}$) (× 10$^2$) (Mean ± SEM, n = 2 − 3)[a] | EF$_{water}$ |
|---|---|---|---|
| I (Control) | None | 15.7 (± 3.1) | 1.00 |
| II (Positive Control) | 5% AC + 20% U | 125.4 (± 26.1)[a] | 7.99 |
| III | 20% SA | 14.0 (± 4.8) | 0.89 |
| IV | 20% U | 18.2 (± 6.5) | 1.16 |
| V | 10% MPG | 39.1 (± 5.2)[c] | 2.49 |
| VI | 10% MPG + 20% SA | 35.6 (± 3.6)[a] | 2.27 |
| VII | 10% MPG + 20% U | 55.5 (± 0.6)[a] | 3.54 |
| VIII | 10% MPG + 31.81% GnHCl | 22.4 (± 1.7) | 1.43 |
| IX | 3.33% MPG + 20% U | 26.7 (± 2.8) | 1.70 |
| X | 10% MPG + 6.67% U | 46.1 (± 3.6)[c] | 2.94 |
| XI | 10% MPG + 10% U + 10% SLS | 8.5 (± 0.5)[b] | 0.89 |
| Control for XI | None | 9.6 (± 0.2)[b] | 1.00 |

[a]Each study was started out with three nails, but if one of the nails cracked or split during the course of the study, then n = 2;
[b]Gel XI was screened using thumbnails due to the limited availability of toenails, hence, its control was also run on thumbnails;
[c]Indicates statistically significantly higher than the control (t-test, α = 0.05).

All enhancers were screened with three replicates; however, in some cases one of the nails split due to weakening of the nail as a result of effective enhancer treatments. Hence, in these cases, n=2. Permeation profiles for gels containing urea alone (IV), MPG alone (V), 10% MPG and 20% urea (VII), and their control (I) are typical for cumulative permeation data and show that steady state is achieved after an initial lag time.

Gel II (positive control) gave the greatest increase in normalized water flux compared with the control (Gel I), resulting in an enhancement factor, EF$_{water}$, of 7.99, confirming that the technique was suitable for screening potential enhancers. The high EF$_{water}$ value is attributed to the fact that the positive control contained a higher amount of water relative to the other gels, and hence, an increased water flux was observed.

Gels containing the keratolytic agents alone, 20% SA (Gel III) or 20% U (Gel IV), were ineffective in enhancing the permeation of water through nails relative to the control (Gel I). Gel V, containing 10% MPG, apparent pH=9.0, resulted in an approximately 2.5-fold increase in normalized water flux that was found to be statistically significant when contrasted with that of the control (t-test, α=0.05). When 10% MPG was combined with 20% SA (Gel VI, apparent pH=4.3), an EF$_{water}$ value of 2.27, similar to that seen with Gel V, containing 10% MPG (EF$_{water}$=2.49), was observed. These results indicate that SA was ineffective in permeation enhancement. Moreover, because the gels containing 10% MPG alone or in combination with SA resulted in similar flux enhancement values, alkaline pH did not appear to favor permeation as compared with acidic conditions. Thus, although a pH of 8–9 has been reported to be optimal for reduction of disulfide linkages (Robbins C R. 1997. Chemical and physical behavior of human hair, 3rd ed. New York: Springer-Verlag. pp. 93–130), pH did not seem to be a major controlling factor for nail penetration enhancement with MPG.

When 20% U was present along with 10% MPG (Gel VII), an approximately four-fold increase in normalized water flux was seen when compared with the control. The enhancement effect of MPG may result from its ability to reduce the disulfide linkages in the nail keratin matrix. Further, its small size and the fact that it is an amino acid may allow incorporation in the nail keratin matrix and exert its effect. Urea acted synergistically with the sulfhydryl-containing reducing agent, MPG, and resulted in an improvement in the EF$_{water}$ value from 2.49 for MPG alone to 3.54 for 10% MPG and 20% U.

The effect of 31.81% GnHCl, equivalent to 20% U on a molar basis, in conjunction with 10% MPG (Gel VIII) was investigated. Urea and GnHCl are structurally similar, however, the slight increase in J* for water observed with Gel VIII was not statistically significant when compared with the control (Gel I) using a t-test at the 0.05 level of significance. Hence, although GnHCl and urea have been reported to have similar denaturing properties (Mathews and van Holde (1990) Biochemistry. Redwood City: The Benjamin/Cummings Publishing Co, pp. 213–215), the results herein indicate that GnHCl is ineffective as a nail penetration enhancer when combined with MPG. It is possible that much higher concentrations of GnHCl may result in improved nail penetration; however, increasing the level of GnHCl above 32% may not be feasible because of solubility limitations.

Having established that the combination of MPG and urea was effective in nail penetration enhancement of water, the effect of concentration of these enhancers was investigated. To study the effect of concentration of MPG, gels were prepared containing 20% U and MPG at three different levels, 0, 3.33, and 10% (Gels IV, IX, and VII, respectively). To study the effect of concentration of U, the gels contained 10% MPG and three different levels of U, 0, 6.67, and 20% (Gels V, X, and VII, respectively). Varying levels of MPG with 20% U indicated that the concentration of mercaptan (MPG) is more important than the urea concentration in penetration enhancement of water. Thus, the profile relating J* of water with the concentration of MPG has a steeper slope compared to that observed with concentration of urea. The importance of MPG concentration is also seen in Table 1, which shows that the $EF_{water}$ value for Gel IX containing 3.33% MPG and 20% U is only 1.70, compared to the $EF_{water}$ value of 3.54 for the gel containing 10% MPG and 20% U (Gel VII). However, in the presence of 10% MPG and 6.67% U (Gel X), the $EF_{water}$ value is 2.94, which is comparable to that seen with 10% MPG and 20% U (Gel VII, $EF_{water}$=3.54). These results indicate that reduction in the mercaptan levels can lower the enhancement effect considerably; however, urea concentration may be decreased without compromising penetration enhancement.

To investigate whether incorporation of a surfactant, SLS, into a gel containing the effective enhancer combination of MPG and urea further improved nail penetration, Gel XI was screened. Thumbnails were used in these studies to compare Gel XI and its control. As seen in Table 1, the control for Gel (XI), run on thumbnails, gave a J* value of $9.6 \times 10^{-2}$ mg $cm^{-1}h^{-1}$, which is considerably lower than the J* value of $15.7 \times 10^{-2}$ mg $cm^{-1}h^{-1}$ for Control (I), run on toenails. This result can be attributed to differences in nail thickness and keratin structure of thumbnails and toenails. Thumbnails were effective barriers to permeation despite their reduced thickness, hence resulting in lower J* values compared to toenails (Malhotra and Zatz (2000) *J Cosmet Sci* 51:367–377).

Gel XI, when compared with its control, resulted in an enhancement factor of 0.89 (Table 1), indicating that the permeation of water was not significantly enhanced when compared with its control (t-test, $\alpha$=0.05). Thus, although SLS has denaturing properties the concentration of 10% used in Gel XI may be insufficient to cause penetration enhancement through nails. The increase in J* values, relative to control formulations observed with gels containing MPG alone or in combination with keratolytic agents, are consistent with other reports in the literature wherein agents such as N-acetyl cysteine and dithiothreitol were shown to increase permeation of model compounds (Kobayashi, et al. (1998) *Chem. Pharm. Bull.* 46(11):1797–1802; U.S. Pat. No. 5,696,164; Soong (1991) Transport properties of drugs and model compounds across the human nail. Ph.D. Dissertation. University of Minnesota).

Pyrithione and its Derivatives. The screening results for gels containing another mercaptan, PTO, and its derivatives are shown in Table 2.

TABLE 2

| Gel | Enhancer | J* (mg $cm^{-1}h^{-1}$) ($\times 10^2$) (Mean ± SEM, n = 2 – 3)[a] | $EF_{water}$ |
| --- | --- | --- | --- |
|  | None (control for gels XII and XIII) | 15.7 (± 3.1) | 1.00 |
| XII | 4% NaPTO | 17.0 (± 1.4) | 1.08 |
| XIII | 10% NaPTO | 10.6 (± 0.98) | 0.68 |
|  | None (control for gels XIV–XVII) | 0.75 (± 0.04)[a] | 1.00 |
| XIV | 2.5% ZnPTO | 0.85 (± 0.15) | 1.13 |
| XV | 10% PTO | 1.94 (± 0.30) | 2.59 |
| XVI | 10% PTO + 20% U (alternate dosing) | 0.82 (± 0.14) | 1.09 |
| XVII | 10% PTO + 10% U | 0.80 (± 0.02) | 1.07 |

[a]Control gel for ZnPTO and PTO formulations was run on two toenails due to limited nail availability.

NaPTO was ineffective at the 4 and 10% level in enhancing permeation of water through nails, relative to the control, thus resulting in $EF_{water}$ values close to 1. ZnPTO and PTO were screened using gels predominantly composed of DMSO. The J* value of $0.75 \times 10^{-2}$ mg $cm^{-1}h^{-1}$ for the control for Gels XIV–XVII was much lower than the J* value of 15.7×10–2 mg cm-1h-1 for control (I). This is primarily because the former gel contained less than 2% water, due to the limited water solubility of ZnPTO and PTO, compared to Gel I, which contained 17% water. Intrinsic differences in nail structure could also contribute to the variability in J* values above. ZnPTO did not enhance water permeation relative to its control ($EF_{water}$=1.13). PTO alone at a concentration of 10% resulted in a 2.6-fold increase in J* for water relative to its control. Thus, 10% PTO may be an effective enhancer of nail permeation. However, the drawback of this compound is its extremely poor solubility in almost all solvents, leading to practical formulation difficulties.

PTO was further investigated in conjunction with urea as a potential penetration enhancer (Gels XVI and XVII). However, when urea was dosed either alternately or concurrently with PTO, the J* values for water did not increase ($EF_{water}$=1.09 and 1.07, respectively, for Gels XVI and XVII). Thus, it was concluded that urea does not improve nail penetration in combination with PTO. A possible explanation for this could be that urea is unable to exert its keratolytic action in a very hydrophobic environment. For Gels XVI and XVII, urea was present in a vehicle containing mostly DMSO and <2% water, which may not be conducive to swelling and hydration of the nail.

Other Mercaptan Compounds. 8-mercaptomenthone and meso-2,3-dimercapto succinic acid, had results similar to that of PTO (Table 3).

TABLE 3

| Gel | Enhancer | J* (mg $cm^{-1}h^{-1}$) ($\times 10^2$) (Mean ± SEM, n = 2 – 3)[a] | $EF_{water}$ |
| --- | --- | --- | --- |
|  | None (control for gel XVIII) | 11.1 (± 1.7)[a] | 1.00 |
| XVIII | 10% 8-mercaptomenthone | 11.7 (± 1.3) | 1.05 |
|  | None (control for gel XIX) | 123.0 (± 20.5)[a] | 1.00 |
| XIX | 10% meso-2,3-dimercapto succinic acid | 107.8 (± 24.0)[a] | 0.88 |
|  | None (control for gel XX) | 122.3 (± 26.7)[a] | 1.00 |
| XX | 10% meso-2,3-dimercatp succinic acid + 20% U | 126.8 (± 0.14)[a] | 1.04 |

[a]These gels were screened using two toenails due to limited nail availability.

10% 8-mercaptomenthone did not enhance penetration of water relative to the control ($EF_{water}$=1.05). The ineffectiveness of 8-mercaptomenthone as a nail penetration enhancer may be due to the nature of the parent molecule. 8-Mercaptomenthone is a terpene derivative. Terpene derivatives are effective skin penetration enhancers and may act by inserting themselves in the lipid bilayers of the skin thereby disturbing their ordered structure (Clarys, et al. (1998) *Eur J Pharm Biopharm* 46:279–283; Gay, et al. (1994) *J Invest Dermatol* 103:233–239). However, the lipid content of the nail plate is very low (Runne and Orfanos (1981) *Curr Probl Derm* 9:102–149). Thus, even if the terpene molecules do result in lipid transitions in the nail, this action may be insignificant to cause major changes in the nail barrier properties.

Gels containing meso-2,3-dimercapto succinic acid either alone or in combination with urea had a high water content of 70–85% due to the good water solubility of these molecules. Hence, the control gel for these enhancers also had a high water content, resulting in large J* values of 123× $10^{-2}$ mg $cm^{-1}h^{-1}$, compared to $15.7 \times 10^{-2}$ mg $cm^{-1}h^{-1}$ for control Gel I. Meso-2,3-dimercapto succinic acid was ineffective in increasing nail permeation of water either when used alone or in combination with urea, thus resulting in $EF_{water}$ values close to 1. In the case of meso-2,3-dimercapto succinic acid, the SH groups are present on adjacent carbon atoms (second and third) and the reduction of disulfide bonds may lead to the formation of a sterically unfavorable product. Moreover, gels containing meso-2,3-dimercapto succinic acid were prepared by adjusting the pH to approximately 9.0. At this pH, the two carboxylic acid groups and the two sulfhydryl groups in the molecule would be ionized. Reports in the literature suggest that compounds such as benzoic acid and pyridine preferentially permeate the nail in the undissociated state (Soong (1991) Transport properties of drugs and model compounds across the human nail. Ph.D. Dissertation. University of Minnesota; Mertin and Lippold (1997) *J Pharm Pharmacol* 49:30–34). Also, because both sulfhydryl groups on adjacent carbon atoms in meso-2,3-dimercapto succinic acid were ionized at pH 9, intramolecular disulfide bond formation could have occurred, thus rendering the molecule ineffective for reduction of disulfide linkages in the nail keratin matrix.

Sulfites and Keratolytic Agents. The screening results for the gels containing 10% sodium metabisulfite ($Na_2S_2O_5$), either alone or in combination with 20% U, are shown in Table 4.

TABLE 4

| Gel | Enhancer | $J^*$ (mg cm$^{-1}$h$^{-1}$) (× 10$^2$) (Mean ± SEM, n = 2 – 3)[a] | $EF_{water}$ |
|---|---|---|---|
| | None (control for gel XXI) | 170.7 (± 10.1) | 1.00 |
| XXI | 10% $Na_2S_2O_5$[a] | 130.9 (± 6.9) | 0.77 |
| | None (control for gel XXII) | 69.7 (± 12.1)[b] | 1.00 |
| XXII | 10% $Na_2S_2O_5$ + 20% U | 83.6 (± 6.3)[b] | 1.20 |

[a]Each mol of sodium metabisulfite ($Na_2S_2O_5$) gives 2 mol of sodium bisulfite (NaHSO3), when in contact with water.
[b]These gels were screened using two toenails due to limited nail availability.

The control formulations exhibited high $J^*$ values because these gels were aqueous in order to dissolve $Na_2S_2O_5$ and urea. It was found that $Na_2S_2O_5$ did not enhance the penetration of water, when used alone or in conjunction with urea ($EF_{water}$ values close to 1). Bisulfites are known to be weaker reducing agents than mercaptans for the disulfide bonds in hair keratin, particularly at room temperature, where extremely long time periods are required to break enough cystine linkages for hair waving (Edman and Klemm (1979) *C & T Magazine* 94:35–38). Thus, reduction by $Na_2S_2O_5$ may have been insignificant to elicit nail penetration enhancement.

The results from the studies described above indicate that the chemical structure of the enhancer is the most important factor determining its ability to enhance nail permeation. Effective penetration enhancement was obtained from a mercaptan derivative of an amino acid, MPG. However, the presence of a SH group was not sufficient to elicit penetration enhancement in all cases. Urea in conjunction with MPG, acted synergistically to increase nail permeation to the greatest extent. Moreover, the effective enhancers resulted in softening of the nail, thus confirming structural changes in the nail plate.

Barrier integrity of nails after enhancer screening studies was evaluated. The normalized water flux values before and after treatment with various chemical modifiers (MPG and keratolytic agents) are shown in Table 5.

TABLE 5

| | $J^*$ (mg cm$^{-1}$h$^{-1}$) (Mean ± SEM, n = 3) | | |
|---|---|---|---|
| Treatment Gel (Enhancer) | Untreated Nail | After Treatment and Washout | $J^*$ treated nail $J^*$ untreated nail |
| I (Control) | 1.01 (± 0.31) | 1.18 (± 0.15) | 1.17 |
| II (Positive Control) | 0.64 (± 0.23)[a] | 3.72 (± 0.90)[a] | 5.33 |
| III (20% SA) | 1.24 (± 0.78) | 1.35 (± 0.58) | 1.09 |
| IV (20% U) | 1.50 (± 0.74) | 1.79 (± 0.76) | 1.19 |
| V (10% MPG) | 1.22 (± 0.56) | 4.01 (± 0.71) | 3.29 |
| VI (10% MPG + 20% SA) | 1.75 (± 0.50)[a] | 3.21 (± 0.71)[a] | 1.83 |
| VII (10% MPG + 20% U) | 1.31(± 0.44)[a] | 4.01(± 0.36)[a] | 3.06 |

[a]Originally three toenails were assigned to these groups, but one nail split during the study, hence data for two nails is shown (n = 2).

Treatment with the positive control (Gel II), 10% MPG (Gel V), and 10% MPG+20% Urea (Gel VII) all resulted in a threefold or greater increase in $J^*$ for water posttreatment and washout. Because these treatments were effective in nail penetration enhancement, it was concluded that these enhancers had irreversibly altered the structure of the keratin matrix. Thus, $J^*$ values remained consistently higher than baseline levels even after washout. Treatment with keratolytic agents alone (salicylic acid, Gel III and urea, Gel IV) did not appear to result in structural changes in the nail keratin as $J^*$ values for water returned to their original levels. Because the other enhancers screened, pyrithione and its derivatives, 8-mercaptomenthone, meso-2,3-dimercapto succinic acid, sodium lauryl sulfate, and sodium metabisulfite, were all ineffective in nail penetration enhancement, their $J^*$ values posttreatment and washout returned to original levels.

Clotrimazole Studies. Clotrimazole, a broad-spectrum antifungal agent, was tested in combination with the composition of the invention. Antifungal permeation was significantly enhanced by a sulfhydryl containing reducing agent (MPG), but not by keratolytic agents alone. The normalized clotrimazole flux ($J^*$), relative flux enhancement ($EF_{clotrimazole}$), and drug uptake by nails after treatment with gels containing 5% clotrimazole, and keratolytic agents either alone or in combination with a mercaptan derivative of an amino acid (MPG), are shown in Table 6.

TABLE 6

| Gel: Enhancer | $J^*$ ($\mu$g cm$^{-1}$day$^{-1}$) | $EF_{clotrimazole}$ | Amount of active in nail ($\mu$g/g) | Relative nail uptake |
|---|---|---|---|---|
| A: None (control) | 3.71 ± 1.80 | 1.00 | 576.6 ± 511.2 | 1.00 |
| B: 20% SA | 2.84 ± 0.42 | 0.77 | 488.6 ± 81.5 | 0.85 |
| C: 10% U | 1.05 ± 0.08 | 0.28 | 2698.0 ± 1110.3 | 4.68 |
| D: 10% MPG | 19.88 ± 4.04* | 5.36 | 3157.2 ± 992.5 | 5.48 |
| E: 10% MPG + 20% SA | 10.09 ± 0.59* | 2.72 | 2596.4 ± 137.6* | 4.50 |
| F:: 10% MPG + 20% U | 33.46 ± 5.93* | 9.02 | 3159.8 ± 438.4* | 5.48 |
| G: 3.33% MPG + 10% U | 6.54 ± 1.42 | 1.76 | 516.5 ± 69.6 | 0.90 |
| H: 10% MPG + 10% U | 28.30 ± 6.16* | 7.63 | 2068.6 ± 472.0 | 3.59 |

*indicates statistically significantly different from control (t-test, $\alpha$ = 0.05).

The $J^*$ values for clotrimazole from gels containing the keratolytic agents alone [20% SA (B) or 10% U (C)] were not statistically significant when compared with the control (A) (t-test, α=0.05). For the gel containing 10% MPG alone (D), a 5-fold increase in normalized clotrimazole flux, relative to control, was observed. These results indicate that the mercaptan compound itself was effective in enhancing permeation of clotrimazole through nails, whereas the keratolytic agents were ineffective when used alone.

When 10% MPG was combined with 20% SA (Gel E), an $EF_{clotrimazole}$ value of 2.72 was observed, which was lower than that seen with the gel containing 10% MPG alone (D). Thus, salicylic acid did not improve permeation enhance of clotrimazole, when present along with the mercaptan compound. However, when 20% urea was used in place of salicylic acid along with 10% MPG (Gel F), a 9-fold increase in normalized clotrimazole flux was seen when compared with the control. Hence, 10% MPG and 20% urea was the most effective enhancer combination for clotrimazole permeation, as was seen in the screening studies with water.

Clotrimazole uptake by nails, calculated from the sum of extractions, indicated that salicylic acid alone (Gel B) was ineffective in promoting penetration of the lipophilic maker, clotrimazole, into nails. Treatment of nails with the gel containing urea alone (C) resulted in an increase relative clotrimazole uptake when compared with the control; however, this increase was not statistically significant (t-test, α=0.05).

Trends for relative clotrimazole uptake for the remaining gels (D-F) were similar to the corresponding effects for flux enhancement. Once again, the highest increase in clotrimazole uptake, 5-fold relative to the control, was observed for the enhancer combination of 10% MPG and 20% U, and this increase was statistically significant (t-test, α=0.05). Thus, as seen in the screening studies with water, the best formulation for enhancement of clotrimazole penetration through nails contained 10% MPG and 20% urea, under infinite dose conditions.

Additional permeation parameters, including $EF_{clotrimazole}$ values, for gels containing the keratolytic agents alone or in combination with the effective enhancer, MPG (Gels A-F) are shown in Table 7.

TABLE 7

| Gel: Enhancer | $EF_{clotrimazole}$ | Additional Permeation Parameters (Mean ± SEM, n = 3) | | |
|---|---|---|---|---|
| | | $P^*$ (cm$^2$day$^{-1}$) (× 10$^5$) | $D$ (cm$^2$day$^{-1}$) (× 10$^4$) | $t_{lag}$ (days) |
| A: None | 1.00 | 7.43 (± 3.60) | 9.06 (± 6.45) | 1.84 (± 0.87) |
| B: 20% SA | 0.77 | 5.68 (± 0.83) | 1.97 (± 0.60) | 2.42 (± 0.37) |
| C: 10% U | 0.28 | 2.11 (± 0.16) | 5.60 (± 2.48) | 1.30 (± 0.76) |
| D: 10% MPG | 5.36 | 39.77 (± 8.08)* | 1.24 (± 0.53) | 4.54 (± 0.55) |
| E: 10% MPG + 20% SA | 2.72 | 20.18 (± 1.18)* | 1.10 (± 0.14) | 3.18 (± 0.20) |
| F: 10% MPG + 20% U | 9.02 | 66.92 (± 11.86)* | 1.33 (± 0.21) | 3.85 (± 0.66) |

*indicates statistically significantly higher than the control (t-test, α = 0.05).

Similar trends to these seen in screening studies with water were observed with clotrimazole. A statistically significant increase in P* values, relative to the control (t-test, α=0.05), was observed for the effective gels containing 10% MPG alone (D), 10% MPG+20% SA (E), and 10% MPG+ 20% U (F). Lag times were increased and diffusion coefficients were decreased in comparison to the control, for effective gels; however, these differences were not statistically significant at the 0.05 level.

To study the effect of concentration of MPG on clotrimazole permeation, gels were prepared containing 10% urea and MPG at three different levels, 0, 3.33, and 10% (Gels C, G, and H, respectively). For effect of concentration of urea on clotrimazole permeation, the gels contained 10% MPG and three different levels of urea, 0, 10, and 20% (Gels D, H, and F, respectively). The normalized fluxes for clotrimazole were linearly dependent on enhancer concentration. In screening studies with water, the concentration of mercaptan (MPG) was more important than the urea concentration in penetration enhancement of clotrimazole. Thus, the slope of the trend line for the effect of varying mercaptan concentration was steeper than the corresponding slope for varying urea levels. As with water, reduction in the mercaptan levels could significantly lower the enhancement effect, however, urea concentration could be decreased without compromising clotrimazole penetration enhancement significantly. Thus, for the gel containing reduced MPG levels (3.33%, Gel G), the $EF_{clotrimazole}$ value was only 1.76; however for reduced urea levels (10%, Gel H), the $EF_{clotrimazole}$ value was 7.63, which is comparable to Gel F containing 20% urea.

The effect of varying levels of clotrimazole on normalized flux (J*) and drug uptake by nails in the presence of the effective enhancers (10% MPG and 20% U) showed a non-linear relationship existed between J* and clotrimazole concentration. The empirical regression equation relating J* and clotrimazole concentration was y=49.30 log(x)+23.67, $R^2$=0.9962. This result differed from that seen for the effect of enhancer concentration on J* of clotrimazole, where a direct linear relationship between these two variable was observed.

Drug uptake by nails, calculated from the sum of the extractions, was directly linearly related to clotrimazole concentration, in the presence of 10% MPG and 20% urea. The regression equation in this case was y=954.45(x), $R^2$=0.9737. The differing relationships between J* on drug uptake and clotrimazole concentration may arise due to the highly complex nature of the keratin matrix. Moreover, these studies were done in the presence of the effective enhancers, MPG and urea, which may have caused varying degrees of change in the keratin structure for different formulations. These results indicate that the enhanced permeation of clotrimazole may not depend linearly on the clotrimazole concentration.

The optimal formulation (10% MPG and 20% urea, Gel F) and the control gel (Gel A), both containing clotrimazole, were studied under conditions of finite dosing, wherein a small volume of 5 μL of the donor gel was applied. The gels were spread in a thin film over the nails and the diffusion cells were not covered during the experiment to allow for a supersaturated layer of gel on the nail surface. Finite dose experiments were carried out to mimic in vivo conditions of use.

Table 8 shows a statistically significant increase (t-test, α=0.05) in normalized clotrimazole flux (J*) for the test relative to the control for infinite and finite dosing.

TABLE 8

| Treatment | J* (μg cm$^{-1}$ day$^{-1}$) | EF$_{clotrimazole}$ | Amount of Active in Nail (μg/g) | Relative Nail Uptake |
|---|---|---|---|---|
| Infinite Dose | | | | |
| Control | 3.71 ± 1.80 | 1.00 | 576.58 ± 511.23 | 1.00 |
| Test[a] | 33.46 ± 5.93* | 9.02 | 3159.79 ± 438.40* | 5.48 |
| Finite Dose | | | | |
| Control | 0.15 ± 0.02 | 1.00 | 72.93 ± 14.32 | 1.00 |
| Test[a] | 1.94 ± 0.27* | 13.40 | 353.06 ± 45.80* | 4.84 |

[a]Test gel contained 10% MPG + 20% urea;
*indicates statistically significantly different from control (t-test, α-0.05).
n = 3.

The absolute values for J* were much higher in infinite dose studies than those seen with finite dosing, due to the much smaller volume of application and thus decreased amounts of drug penetration under finite dose conditions. However, the relative flux enhancement under finite dose conditions (EF$_{clotrimazole}$=13.40) was comparable to that seen under infinite dose conditions (EF$_{clotrimazole}$=9.02). Also, the test gel resulted in a 5-fold greater drug uptake by nails as compared with the control under finite dose conditions, which was similar to the relative nail uptake with infinite dosing.

The normalized water flux values before and after treatment with various antifungal gels containing chemical modifiers (MPG and keratolytic agents) are shown in Table 9.

TABLE 9

| Antifungal Gel (Enhancer) | J*(mg cm − 1h − 1) (Mean ± SEM, n = 3) | | J* treated nail untreated nail |
|---|---|---|---|
| | Untreated Nail | After treatment and washout | |
| Infinite Dose | | | |
| A (Control) | 0.68 ± 0.18 | 1.04 ± 0.114 | 2.03 |
| B (20% SA) | 0.68 ± 0.06 | 1.10 ± 0.07* | 1.65 |
| C (10% U) | 0.68 ± 0.05 | 1.02 ± 0.02* | 1.52 |
| D (10% MPG) | 0.69 ± 0.09 | 2.77 ± 0.23* | 4.17 |
| E (10% MPG + 20% SA) | 0.67 ± 0.02 | 1.76 ± 0.12* | 2.62 |
| F (10% MPG + 20% U) | 0.70 ± 0.08 | 2.98 ± 0.15* | 4.33† |
| Finite Dose | | | |
| A (Control) | 0.68 ± 0.04 | 1.06 ± 0.10* | 1.55 |
| F (10% MPG + 20% U) | 0.70 ± 0.11 | 1.40 ± 0.10* | 2.10 |

*indicates statistically significantly different from baseline J* value (t-test, α − 0.05);
†indicates statistically significantly higher than J*$_{untreated\ nail}$ of control (t-test, α − 0.1).

Under infinite dose conditions, treatment with all antifungal gels, except the control, resulted in a statistically significant increase in J* for water post treatment and washout relative to baseline J* values (t-test, α-0.05). These results suggest that clotrimazole itself may have affected the nail structure, since ineffective gels, containing salicylic acid (B) and urea (C), also resulted in a compromised barrier. Moreover, all antifungal studies were done on fingernails, as opposed to toenails used for screening studies with water. Since fingernails are thinner than toenails, clotrimazole treatment itself may have resulted in some structural changes in the keratin matrix. The ratio of J* for treated nail to J* for untreated nail for the most effective gel containing 10% MPG+20% U (F) was statistically significantly higher than this ratio for the control formulation (t-test, α-0.1). These results indicated that this effective enhancer gel resulted in irreversible changes in the keratin matrix of nails.

For finite dose treatment, the control and test gel both resulted in a statistically significant increase in J* for water post treatment relative to baseline J* values (t-test, α-0.05). These results, again, indicated that clotrimazole itself may effect nail structure. However, the J* ratio for treated to untreated nail for the test gel was not significantly different from the J* ratio for the control gel. Finite dose studies had a small volume of application and therefore, the test gel may not have affected nail structure more than the control gel.

Water and Clotrimazole Comparisons. Penetration enhancement by the mercaptan compound, MPG, and the keratolytic agents, salicylic acid and urea, for the two marker molecules, water and clotrimazole, is summarized in Table 10.

TABLE 10

| Enhancer | J*(μg cm$^{-1}$day$^{-1}$) (Mean ± SEM, n = 2 − 3)[a] | | Normalized Flux Enhancement | |
|---|---|---|---|---|
| | Water | Clotrimazole | EF$_{water}$ | EF$_{clotrimazole}$ |
| None (control) | 3770.9 ± 744.0 | 3.71 ± 1.80 | 1.00 | 1.00 |
| 20% SA | 3351.3 ± 1149.6 | 2.84 ± 0.42 | 0.89 | 0.77 |
| 10% or 20% U[b] | 4375.5 ± 1567.2 | 1.05 ± 0.08 | 1.20 | 0.28 |
| 10% MPG | 9382.4 ± 1248.0* | 19.88 ± 4.04* | 2.49 | 5.36 |
| 10% MPG + 20% SA | 8541.4 ± 854.4[a]* | 10.09 ± 0.59* | 2.27 | 2.72 |
| 10% MPG + 20% U | 13330.6 ± 141.6[a]* | 33.46 ± 5.93* | 3.67 | 9.02 |

[a]The study was started out with 3 nails, but one nail cracked or split during the study, hence n = 2;
[b]10% urea was used with clotrimazole gels, while 20% urea was used with water gels;
*indicates statistically significantly different from the control (t-test, α = 0.05).

The individual fluxes and relative flux enhancement values (EF$_{water}$ and EF$_{clotrimazole}$) are shown. The absolute J* values for water were much higher than for clotrimazole because water is a much smaller, hydrophilic molecule compared to clotrimazole. Various enhancer treatments gave qualitatively similar results for both water and clotrimazole. Thus, with both markers, there was a statistically significant increase in J*, relative to control, observed for gels containing 10% MPG, 10% MPG+20% SA, and 20% MPG+20% U using a t-test at the 0.05 level of significance. Also, the gel with 10% MPG and 20% urea resulted in the greatest increase in permeation for each marker. However, the relative flux enhancements for water and clotrimazole were quantitatively different. Therefore, while treatment with 10% MPG resulting in a 2.5-fold increase in J* for water, a greater than 5-fold increase in J* for clotrimazole was observed. Similarly, a greater degree of enhancement in clotrimazole permeation was observed upon treatment with 10% MPG and 20% urea, as compared to water permeation enhancement (EF$_{water}$=3.67 and EF$_{clotrimazole}$=9.02).

Additional comparative results for water and clotrimazole permeation from the control and optimal formulation, 10% MPG and 20% urea, are shown in Table 11.

TABLE 11

| Gel | Relative Flux Enhancement | | Drug Uptake | | Relative Drug Uptake | |
|---|---|---|---|---|---|---|
| | $EF_{water}^a$ | $EF_{clotrimazole}^b$ | Water ($\mu g/cm^3$)[a,c] | Clotrimazole ($\mu g/g$)[b] | Water[a] | Clotrimazole[b] |
| Control | 1.00 | 1.00 | 4128.8 (±534.5) | 576.6 (±511.2) | 1.00 | 1.00 |
| Test[d] | 3.92* | 9.02* | 9857.5 (±4413.9) | 3159.8 (±438.4)* | 2.36 | 5.48* |

[a]Water permeation studies were done on thumbnails;
[b]Clotrimazole permeation studies were done on thumbnails and other fingernails;
[c]Uptake was calculated from the drug present in the extractions divided by the product of diffusion cell area and nail thickness, assuming lateral diffusion is negligible;
[d]Test gel contained 10% MPG + 20% urea;
*indicates statistically significantly different from the control (t-test, $\alpha = 0.05$).

The permeation for both markers was performed on fingernails, thumbnails for water permeation and thumbnails and other fingernails for clotrimazole permeation. The normalized water flux was about 4-fold higher than the control from gels containing 10% MPG+20% urea for studies on thumbnails, similar to the 4-fold enhancement observed when toenails were used. Clotrimazole flux enhancement was about 9-fold higher than the control. The absolute values for water uptake were much higher than for clotrimazole uptake. Although the test formulation resulted in an approximately 2-fold increase after uptake by nails, this increase was not statistically significant (t-test, $\alpha=0.05$). However, as before, the effect of enhancers on clotrimazole uptake was much more pronounced. Thus, an approximately 5-fold increase in clotrimazole uptake was observed, and this increase is statistically significant when compared with the control (t-test, $\alpha=0.05$). These results suggest that enhancers such as MPG and urea can improve the penetration of larger, lipophilic molecules more dramatically than smaller, hydrophilic compounds, and thus are particularly useful in antifungal formulations for treatment of nail infections and the like.

The composition of the present invention may be used prior to or in conjunction with active agents or drugs for treating diseased nails, nutrients or nail conditioners which may be used to improve damaged nails or maintain healthy nails, and nail growth promoters which may be used on damaged or healthy nails. The active agents include but are not limited to antifungal drugs used to treat onychomycosis, antibiotics (or antiseptics) for bacterial infection of nails, and antipsoriatic drugs for psoriatic nail treatment. Examples of antifungal drugs include but are not limited to miconazole, econazole, ketoconazole, itraconazole, fluconazole, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts. The preferred antifungal drugs are an azole, an allylamine, or a mixture thereof. Preferred azoles are selected from the group consisting of itraconazole, ketoconazole, miconazole, econazole, fluconazole, voriconazole, clotrimazole, butenafine, undecylenic acid, clioqinol, and their pharmaceutically acceptable salts. Preferred allylamines are selected from the group consisting of terbinafine, naftifine and mixtures thereof.

Examples of antibiotics (or antiseptics) include but are not limited to mupirocin, neomycin sulfate, bacitracin, polymyxin B, 1-ofloxacin, tetracyclines (chlortetracycline hydrochloride, oxytetracycline hydrochloride and tetracycline hydrochloride), clindamycin phosphate, gentamicin sulfate, benzalkonium chloride, benzethonium chloride, hexylresorcinol, methylbenzethonium chloride, phenol, quaternary ammonium compounds, triclocarbon, triclosan, tea tree oil, and their pharmaceutically acceptable salts. Preferred antibiotics and antiseptics include mupirocin, neomycin sulfate, bacitracin, polymyxin B, 1-ofloxacin, tetracyclines, benzalkonium chloride, benzethonium chloride, triclocarbon, and triclosan.

Examples of antipsoriatic drugs include but are not limited to corticosteroids (e.g., betamethasone dipropionate, betamethasone valerate, betamethasone benzoate, clobetasol propionate, diflorasone diacetate, halobetasol propionate, budesonide, chloquinaldol, clioquinol, amcinonide, alclometasone dipropionate, beclomethasone dipropionate, bendacort, clobetasol butyrate, desonide, dexamethasone, dichlorisone, diflorasone diacetate, diflucortolone valerate, difluprednate, fluazacort, fluclorolone, desoximetasone, fluocinonide, fluocinolone acetonide, fludroxycortide, flumethasone pivalate, fluocortolone, fluorometholone, flupamesone, fluprednidene, fluprednidene acetate, halometasone, hydrocortamate, prednicarbate, prednisolone, prednisone, tixocortol, halcinonide, triamcinolone acetate, hydrocortisone, hydrocortisone verlerate, hydrocortisone butyrate, aclometasone dipropionate, flurandrenolide, mometasone furoate, methylprednisolone acetate), calcipotriene and anthraline. Preferred antipsoriatic drugs include betamethasone dipropionate, betamethasone valerate, and clobetasol propionate. The corticosteroids may be present either as free alcohols or in the form of their esters.

When the active agents are nail growth promoters, such agents include but are not limited to minoxidil, minoxidil sulfate, retinoids, cysteine and acetyl cysteine, methionine, glutathione, biotin, finasteride and ethocyn, as well as pharmaceutically acceptable salts of these compounds. Preferred growth promoters include minoxidil, minoxidil sulfate, retinoids, cysteine and acetyl cysteine. Particularly preferred nail growth promoters are 2% minoxidil, 2% minoxidil sulfate, and 0.1% retinol.

When the active agents include nutrients, they include but are not limited to vitamins, amino acids, and their derivatives. Examples of such agents include, but are not limited to, vitamin B complex: thiamine, nicotinic acid, biotin, pantothenic acid, choline riboflavin, vitamin $B_6$, vitamin $B_{12}$, pyridoxine, inositol, carnitine; ascorbic acid, ascorbyl palmitate, vitamin A, vitamin K, vitamin E, vitamin D, cysteine and N-acetyl cysteine, herbal extracts, and their derivatives.

When the active agents include nail conditioners they include, but are not limited to, mineral-containing compounds, flavonoids and retinoids. These nail conditioners improve general nail conditions, such as strengthening the nails to prevent nail chipping and cracking, and to beautify the nails. Examples of such agents include but are not limited to calcium pantothenate, calcium carbonate, and calcium gluconate. Examples of retinoids include, but are not limited to, retinol (Vitamin A alcohol), retinal (Vitamin A aldehyde), retinyl acetate, retinyl palmitate, retinoic acid, 9-cis-retinoic acid and 13-cis-retinoic acid. When retinoids are the active agents, the concentration of retinoids is from about 0.01% to about 0.5%, preferably, from about 0.05 to about 0.1%. Examples of flavonoids include, but are not limited to, naringenin, quercetin, catechins (e.g., epigallocatechin gallate), theaflavins, robustaflavone, hinokiflavone, amentoflavone, agathisflavone, volkensiflavone, morelloflavone, rhusflavanone, and succedangeaflavanone.

Overall, the preferred active agents are miconazole nitrate, itraconazole, econazole nitrate, ketoconazole, clotrimazole, and terbinafine. The active agent is present in about 0.05% to about 10% w/w, preferably, from about 0.1% to about 5%, more preferably from about 0.5% to about 2%.

Aside from the MPG, urea and the active agent, the compositions of this invention may include other substances, such as preservatives, cosmetic additives, antioxidants, chelating agents, opacifiers, and pigment flakes. Examples of such agents include, but are not limited to, benzoic acid, benzyl alcohol (as preservative), glycerol, propylene glycol as emollient, butylated hydroxy toluene, butylated hydroxyanisole, ascorbic acid, ascorbyl palmitate, N-acetyl cysteine as antioxidant, citric acid, edetic acid and its sodium salts as chelating agent.

An example of a topical formulation comprises 1% clotrimazole as active agent, 10% MPG and 20% urea as nail penetration enhancers, and 0.1% butylated hydroxy toluene as antioxidant.

The invention includes a lacquer composition comprising at least one active agent, at least one penetration enhancer, at least one volatile solvent, and at least one polymeric film former. As defined herein, lacquer refers to a liquid substance which typically dries to form a continuous or a non-continuous film by evaporation of the solvent. A polymeric film former refers to a polymer which may be added to a volatile solvent and other substances to form a polymeric solution which may be applied to form a film. Examples of polymeric film formers include, but are not limited to, acrylic copolymers/acrylic polymers, (such as CARBOSET™ or AVALURE™ polymers, made by B F Goodrich); polymers of methacrylic acid and its esters (such as EUDRAGIT™ polymers: S, L, RS and RL series, made by Rohm Pharma); cellulose polymers, nitrocellulose, methyl cellulose, ethyl cellulose, cellulose acetates (such as cellulose triacetate, cellulose acetate butyrate); nylon, polyvinyl acetate, polyvinyl acetate phthalate, formaldehyde resin, and polymer blends of the aforementioned polymers. Preferred polymeric film formers are selected from the group consisting of acrylic copolymers/acrylic polymers, (such as CARBOSET™ or AVALURE™ polymers, made by B F Goodrich); polymers of methacrylic acid and its esters, (such as EUDRAGIT™ polymers: S, L, RS and RL series, made by Rohm Pharma). An example of a volatile solvent includes, but is not limited to, water.

Lacquers may have different viscosities. The viscosity of the lacquer is related to the thickness of the film that will be left on a surface once the volatile solvent has evaporated. If one desires a thick and viscous lacquer, which will deposit a thick film on a surface, the concentration of the polymeric film former should be about 0.1% to about 30%, preferably from about 0.5% to about 15% of the total composition. If one desires a thin lacquer which will deposit a thin film on a surface, the concentration of the polymeric film former should be about 0.1% to about 15%, preferably about 0.5% to about 5.0% of the total composition.

The lacquers of the invention may have other additives such as plasticizers (to maintain the pliability of the film formers), non-volatile drug solubilizers, cosmetic additives, and pharmaceutical additives.

When plasticizers and non-volatile drug solubilizers are used, examples of these substances include, but are not limited to, phthalate esters (e.g., dibutyl phthalate), citrate esters, triacetin, isopropyl myristate, N-methyl-2-pyrrolidone, fatty acids and fatty acid esters, propylene glycol, butylene glycol, hexylene glycol, propylene carbonate, poly-propylene glycol, methoxypolyethylene glycol, polyethylene glycol, glycerin. When plasticizers are used they are preferably about 0.001 to about 10% by weight of the total composition.

Pharmaceutical additives include but are not limited to antioxidants and chelating agents. Examples of antioxidants include, but are not limited to, butylated hydroxy toluene, butylated hydroxyanisole, ascorbic acid, ascorbyl palmitate, N-acetyl cysteine. Examples of chelating agents include but are not limited to citric acid, edetic acid and its sodium salts. Cosmetic additives include, but are not limited to, coloring agents, fragrance, pigments, as well as powders of silica, zinc oxide, and titanium oxide.

The typical topical formulation containing the lacquer composition comprises 1% clotrimazole as active agent, 10% MPG and 20% urea as nail penetration enhancers, 15% acrylic polymer (CARBOSET™ or AVALURE™ AC 315) as film former, 0.7% isopropyl myristate as non-volatile drug solubilizer, 0.1% butylated hydroxy toluene as antioxidant, 0.1% citric acid, and 43% ethyl alcohol and 40% ethyl acetate as volatile solvents.

The invention includes a method of treating disease infected human nails by topically applying either a composition comprising at least one active agent, MPG, and urea or a lacquer composition comprising at least one active agent, at least one volatile solvent, MPG, urea, and at least one polymeric film former.

Any method of physically transferring the composition of the invention to the nail may be used. Such methods include, but are not limited to, painting the composition or lacquer on the surface of the nail; spraying the composition or lacquer using a spray pump, and combining the composition or lacquer with a propellant so that it is sprayed on the nail as an aerosol.

Typically for the treatment of nail diseases, the composition or lacquer is initially applied for once or twice per day and may be reduced to once or twice a week depending upon the intensity and resilience of the underlying infection.

As used herein, disease refers to fungal diseases, bacterial diseases and psoriasis. Fungal diseases of the human nail that can be treated in accordance with the invention include, but are not limited to, onychomycosis. This disease is typically caused by an infection of *Epidermophyton floccosum*; several species of *Trichophyton*, such as *T. rubrum*, *T. megninii*, *T. schoenleinii*, *T. tonsurans*, *T. mentagrophytes*; yeast, such as *Candida albicans*; molds, such as *Scopulariopsis cephalosporium* and *Aspergillus fusarium*; or *Hendersonula toruloideo*.

Fungal infections which may be treated using the compositions and methods of the invention are usually characterized by tarnished white, yellowed, or blackened nails. The nails will usually pull away from the pink nail bed along the sides or out edges, and infections are usually exacerbated by hot, damp conditions inside the shoes or in environments where hands or feet are continually exposed to moisture. The fungal infections are most commonly found in the toenails and may spread from toe to toe, foot to foot, and foot to hand. Diagnosis of the fungal infections may be microscopic identification and/or culture of the infected areas.

Specific infections which may be treated by the compositions and methods of the invention include distal subungual onychomycosis, caused by infection with *C. trichophyton, Scopularosis,* and *Aspergillus*); superficial white onychomycosis, caused by *T. mentagrophytes*; proximal white subungual onychomycosis, caused by *Trichophyton* species; total secondary dystrophic onychomycosis, caused by yeast and *Trichophytons*; and total dystrophic primary onychomycosis, caused by *Candida* species.

The topical treatment of the invention may be employed in combination with systemic treatment. For example, an antifungal drug, such as, itraconazole, terbinafine, griseofulvin or other antifungal drugs, may be given orally over a period of time. This time period may be concurrently during the entire topical treatment regimen, or concurrently during a portion (usually the latter phase) of the topical treatment regimen, or following the topical treatment.

The invention is described in greater detail by the following non-limiting example.

EXAMPLE 1

Materials

Tritiated water ($^3H_2O$) (specific activity of 1 µCi/mg) was obtained from NEN™ Life Sciences Products (Boston, Mass.). Tritiated clotrimazole, [3H]-Clotrimazole, (specific activity of 8 Ci/mmol) was obtained from Moravek Biochemicals, Inc. (Brea, Calif.). Hydroxyethyl cellulose (HEC, NATROSOL®), hydroxypropyl cellulose (HPC, KLUCEL®, Aqualon Co., Wilmington, Del.), and polyethylene glycol-20-oleyl ether (PEG-20-oleyl ether, Croda, Inc., Parsippany, N.J.) were used as received. Sodium pyrithione was received from Arch Chemicals Inc. (Norwalk, Conn.). All drugs including N-acetyl-1-cysteine, N-(2-mercaptopropionyl) glycine (MPG), pyrithione, and its zinc derivative, 8-mercaptomenthone, meso-2,3-dimercapto succinic acid, clotrimazole, sodium metabisulfite, and salicylic acid were obtained from Sigma-Aldrich Chemical Co. (St. Louis, Mo.). All other laboratory chemicals (ACS grade or better), including Scintiverse I, urea, sodium lauryl sulfate, and propylene glycol were obtained from Fisher Scientific (Springfield, N.J.) and used as received. Ethanol (200 Proof) was obtained from Aaper Alcohol and Chemical Company (Shelbyville, Ky.).

EXAMPLE 2

Preparation of Nails

Frozen human toenails and fingernails were obtained from tissue banks based on a protocol for size, patient history, etc. The nails were thawed at room temperature for 1 hour, and the adhering skin and tissue was removed with a pair of scissors and a scalpel. The nails were cleaned by rinsing them in a mild detergent solution (1% solution of a standard liquid soap containing sodium and potassium dodecyl benzene sulfonate and ammonium laureth sulfate), followed by two rinses in deionized water (DI water). The thickness of the nails was measured with a micrometer, and the nails were immersed in 10 mL of DI water for 24 hours just prior to use to allow complete hydration and bring all the nails to the same condition for valid comparisons (Kobayashi, et al. (1998) *Chem. Pharm. Bull.* 46(11):1797–1802; Walters, et al. (1981) *J Invest Dermatol* 76:76–79; Mertin and Lippold (1997) *J Pharm Pharmacol* 49:30–34).

EXAMPLE 3

Nail Permeation Cells

Franz-type diffusion cells (Crown Glass Co., Somerville, N.J.), specially designed to hold the human nail were used (Malhotra and Zatz (2000) *J Cosmet Sci* 51:367–377). The cleaned, trimmed nails were clamped into the diffusion cells. The area of the cell available for permeation was 0.2749 cm². A circulating water bath maintained the temperature of the receptor compartment at 37° C. Magnetic stirrer bars ensured stirring throughout an experiment.

EXAMPLE 4

Donor Formulations

Enhancers tested and their concentrations are shown in Table 12.

TABLE 12

| Class of Enhancer | Enhancer(s) | Gel |
|---|---|---|
| Control | None | I |
| Positive control | 5% AC[a] + 20% U[b] | II |
| Keratolytic agents | 20% SA[c] | III |
|  | 20% U | IV |
| Mercaptan derivatives of amino acids | 10% MPG[d] | V |
|  | 10% MPG + 20% SA | VI |
|  | 10% MPG + 20% U | VII |
|  | 10% MPG + 31.81% GnHCL[e] | VIII |
|  | 3.33% MPG + 20% U | IX |
|  | 10% MPG + 6.67% U | X |
|  | 10% MPG + 10% U + 10% SLS[f] | XI |
| Pyrithione and its derivatives | 4% NaPTO[g] | XII |
|  | 10% NaPTO | XIII |
|  | 2.5% ZnPTO[h] | XIV |
|  | 10% PTO[i] | XV |
|  | 10% PTO + 20% U (alternate dosing) | XVI (a&b) |
|  | 10% PTO + 10% U | XVII |
| Other mercaptans | 10% 8-mercaptomenthone | XVIII |
|  | 10% Succimer[j] | XIX |
|  | 10% Succimer + 20% U | XX |
| Bisulfite | 10% $Na_2S_2O_5$[k] | XXI |
|  | 10% $Na_2S_2O_5$ + 20% U | XXII |

[a]AC = N-acetyl-1-cysteine,
[b]U = urea,
[c]SA = salicyclic acid,
[d]MPG = N-(2-mercaptopropionyl) glycine,
[e]GnHCl = guanidine hydrochloride,
[f]SLS = sodium lauryl sulfate,
[g]NaPTO = sodium pyrithione,
[h]ZnPTO = zinc pyrithione,
[i]PTO = pyrithione,
[j]Succimer = meso-2,3-dimercapto succinic acid,
[k]$Na_2S_2O_5$ = sodium metabisulfite.

Gels were prepared containing enhancers either alone or in combination with each other, in a vehicle that was either aqueous, hydroalcoholic, or one containing dimethylsulfoxide (DMSO). The nature of the vehicle was dependent on the solubility characteristics of the enhancer. The polymer used as the gelling agent was HPC for the hydroalcoholic and DMSO containing gels. HEC was used as the gelling agent for the aqueous gels. An appropriate control gel was prepared for each of the enhancers studied. The control gel did not contain the enhancer, but had a vehicle of the same composition (ingredients in the same proportions) as the test formulation with enhancer, for example, Gel (I) was used as a control for Gels (III)–(XI). A positive control (Gel II), based on the U.S. Pat. No. 5,696,164 containing 5% N-acetyl-1-cysteine (AC) and 20% U was also studied. Representative formulations for gels containing the keratolytic agent, urea, alone (Gel IV), the mercaptan compound, MPG, alone (Gel V), a combination of MPG and urea (Gel VII), and a control (Gel I) are shown in Table 13.

TABLE 13

| Ingredients | Composition (%) | | | |
|---|---|---|---|---|
| | Gel I | Gel IV | Gel V | Gel VII |
| Alcohol | 60.00 | 47.63 | 53.82 | 41.45 |
| Propylene glycol | 20.00 | 9.52 | 17.94 | 8.29 |
| MPG | — | — | 10.00 | 10.00 |
| Urea | — | 20.0 | — | 20.0 |
| HPC (KLUCEL ®) | 3.00 | 3.0 | 3.0 | 3.0 |
| DI water | 17.00 | 19.85 | 15.24 | 17.26 |

All gels were prepared using the same general procedure. Briefly, the enhancers were dissolved in the appropriate vehicle with vortex agitation. All the gels were spiked with $^3H_2O$ so as to obtain a "hot": "cold" ratio of 1:1000, with the exception of PTO and ZnPTO gels (Gels XIV–XVII), which had a spiking ratio of 1:400. HEC/HPC was added to the mixture, and gel formation was allowed by agitating on a mechanical shaker bath at 37° C. overnight. The apparent pH of the gels was measured. Prior to use, three 10 μL aliquots of the gel were analyzed by Liquid Scintillation Counting (LSC) to validate uniformity of spiking.

EXAMPLE 5

Enhancer Screening Studies

Each gel formulation was screened using three replicates. Excised human toenails were used to screen all the gels, except for the gel containing the surfactant (XI), where thumbnails were used due to the limited availability of toenails. Before the start of the study, a baseline normalized water flux, J*, defined as the product of flux (J) and nail thickness, was established for all the nails. This was accomplished by monitoring the permeation of $H_2O$ through the nails from aqueous gels, followed by a washout procedure. The nails were assigned to different treatment groups, comprising three nails each, such that the mean normalized water flux for each group was approximately equal.

Hydrated, trimmed nails were clamped in the diffusion cells and the receptor compartment was filled with the receptor fluid which was water containing 0.5% PEG-20-oleyl ether, a wetting agent that helped to remove entrapped air bubbles and was nondestructive to nails (Bronaugh and Stewart (1984) *J Pharm Sci* 73:1255–1258). A temperature of 37° C. and constant stirring was maintained throughout each study. The cells were left uncovered for 1 hour prior to application of the donor formulation to allow the top surface of the nails to dry out. The diffusion cells were then dosed with 200 μL of the gel formulations under investigation and covered with PARAFILM™. Samples were drawn every 8 hours over a period of 6–14 days. Initial studies were run for 2 weeks to establish when steady state conditions were reached, and based on these earlier studies, the overall duration was later reduced to 6 days. At each sampling time, the entire contents of the receptor compartment were removed and replenished with an equal volume of fresh receptor fluid. Additionally, at each sampling time, the donor gel adhering to the nail from a previous application was wiped off completely using tissues dipped in 65% alcohol. The cells were redosed with 200 μL of the donor gel, and were again covered. Due to solubility constraints, the combination of 10% PTO and 20% U was screened by alternately dosing with two separate gels, XVIa and XVIb, containing 10% PTO and 20% urea, respectively.

At the end of the study, the nails were removed from the diffusion set up and rinsed repeatedly in 65% alcohol (DMSO for the PTO and ZnPTO formulations, XIV–XVII), followed by DI water, for radioactivity and residual enhancer extraction. The extractions were carried out by shaking on a mechanical shaker bath at 25° C. for successive 24-hour periods, until the radioactive counts from the extractions approached blank values.

EXAMPLE 6

Donor Formulations for Antifungal Studies

Infinite Dose Studies. To study the effect of various enhancers on antifungal permeation, gels were prepared containing 5% clotrimazole and the different chemical modifiers (Table 14).

TABLE 14

| Class of Enhancer | Enhancer(s) | Gel |
|---|---|---|
| Control | None | A |
| Keratolytic Agent | 20% SA | B |
| | 10% U | C |
| Mercaptan derivatives of amino acids | 10% MPG | D |
| | 10% MPG + 20% SA | E |
| | 10% MPG + 20% U | F |
| | 3.33% MPG + 10% U | G |
| | 10% MPG + 10% U | H |

Abbreviations:
SA = salicylic acid;
U = urea;
MPG = N-(2-mercaptopropionyl) glycine.

Since MPG and the keratolytic agents were soluble in a hydroalcoholic medium, all the gels (A–H) were prepared in a vehicle comprising ethanol, propylene glycol, and water. The polymer used as the gelling agent was HPC. Gels A–H had similar compositions to the gels used in enhancer screening studies with water as a probe, however, in this case the gels each contained 5% clotrimazole. Representative formulations for gels containing urea alone (Gel C), MPG alone (Gel D), a combination of MPG and urea (Gel F), and a control (Gel A) are shown in Table 15.

TABLE 15

| Ingredients | Composition (%) | | | |
|---|---|---|---|---|
| | Gel A | Gel C | Gel D | Gel F |
| Clotrimazole | 5.00 | 5.00 | 5.00 | 5.00 |
| Alcohol | 60.00 | 53.47 | 53.47 | 40.39 |
| Propylene glycol | 20.00 | 10.69 | 17.82 | 8.08 |
| MPG | — | — | 10.00 | 10.0 |
| Urea | — | 10.0 | — | 20.0 |
| HPC (KLUCEL ®) | 3.00 | 3.0 | 3.0 | 3.0 |
| DI water | 11.8 | 17.64 | 10.51 | 13.33 |
| BHT | 0.10 | 0.10 | 0.10 | 0.10 |
| Disodium EDTA | 0.10 | 0.10 | 0.10 | 0.10 |
| Apparent pH | 7.50 | 8.18 | 3.22 | 4.50 |

Abbreviations:
MPG = N-(2-mercaptopropionyl) glycine;
BHT = butylated hydroxytoluene;
EDTA = ethylenediamine tetra acetic acid.

The gels were prepared using the same general procedure as that used for the enhancer screening studies. Briefly, clotrimazole and the enhancers were dissolved in the hydroalcoholic vehicle with vortex agitation. Butylated hydroxy toluene (BHT) was added as an antioxidant to prevent oxidation of MPG. Disodium EDTA was also added as a chelating agent. All gels were spiked with [3H]-Clotrimazole to obtain a ratio of "hot":"cold" drug of approximately 1:60,000. This very dilute spiking ratio was sufficient due to the high specific activity of [3H]-Clotrimazole (8 Ci/mmol). HPC was added to the mixture, and gel formation was allowed by agitating on a mechanical shaker bath at 37° C. overnight. The apparent pH of the gels was measured. Prior to use, three 10 μL aliquots of the gels were analyzed by LSC to validate uniformity of spiking.

To study the effect of concentration of clotrimazole on nail permeation of gels containing enhancers, additional formulations were prepared containing 0.5% and 2% clotrimazole in conjunction with the effective enhancer combination of 10% MPG and 20% urea. These were studied along with the gel containing 5% clotrimazole and the same enhancers (Gel F, Table 14).

Finite Dose Studies. Formulations similar to gels A (control) and F (10% MPG+20% Urea), shown in Table 14 and Table 15, were prepared for finite dose studies. Clotrimazole was present in a concentration of 5%, as for infinite dose studies. However, in this case a higher spiking ratio of 1:40,000 was used.

EXAMPLE 7

Receptor Fluid Studies for Antifungal Studies

The choice of receptor fluid depends on both physiologic considerations, and solubility requirements to achieve sink conditions. Clotrimazole has a limited solubility in water (<0.01 mg/mL), but is very soluble in alcohol (95 mg/mL) and some other organic solvents, at 25° C. (Hoogerheide and Wyka (1982) In: Analytical profiles of drug substances, Vol. 11, K. Florey (ed.), Academic Press, New York, pp. 225–255). For the present invention differing concentrations of the nonionic surfactant PEG-20-oleyl ether (HLB=16) were used. This surfactant at a concentration of 6% was reported to be a receptor fluid of choice for in vitro skin permeation studies with highly hydrophobic molecules (Bronaugh and Stewart (1984) *J Pharm Sci* 73:1255–1258). Moreover, when this surfactant solution was used as the receptor fluid, the barrier integrity of the skin was retained as assessed by monitoring the permeation of control substances such as cortisone, urea, and water.

Aqueous solutions of PEG-20-oleyl ether in concentrations of 0.5%, 1%, 2%, and 5% were prepared. Excess clotrimazole was added to vials containing 10 mL of surfactant solution. For each surfactant concentration, the solubility determination was done in triplicate. The vials were agitated in a mechanical shaker bath (Precision Scientific, Chicago, Ill.) maintained at 37° C. for 24 hours. The vials were then centrifuged (Fisher Scientific, Springfield, N.J.) at 4600 rpm for 30 minutes at 25° C. The supernatant was analyzed for drug concentration by High Performance Liquid Chromatography (HPLC).

The HPLC conditions were adapted from well known methods, for example Hoogerheide, et al. ((1981) *J Assoc Off Anal Chem* 64:864–869) and Rifai, et al. ((1995) *Clin Chem* 41:387–391). The HPLC analysis was performed using a Waters 600E System Controller Pump, Waters 717 Autoinjector, Waters 486 Tunable Absorbance Detector, and Waters 700 Data Module Integrator. A reverse-phase C-18 column (Waters Novapak, 3.9×150 mm, 4μ) was used. The mobile phase consisted of a mixture of 0.025M dibasic potassium phosphate (pH adjusted to approximately 6.3 with o-phosphoric acid) and HPLC grade methanol in the ratio 1:3. A flow rate of 1 mL/minute was maintained and the detector wavelength was set at 254 nm.

Standard solutions of clotrimazole in mobile phase were prepared in the concentration range of 5–200 μg/mL. The injection volume of standard and sample solutions was 20 μL. The run time was 7.0 minutes and clotrimazole had a retention time of 5.74 minutes.

The chromatography conditions yielded a linear standard curve ($R^2$=0.9995). From the standard curve, the solubility of clotrimazole in different concentrations of PEG-20-oleyl ether was quantitatively determined. The solubility results are summarized in Table 16.

TABLE 16

| Concentration of PEG-20-oleyl ether | Solubility of clotrirnazole (μg/mL) (Mean ± SEM, n = 3) |
| --- | --- |
| 0.5% | 75.16 (±7.81) |
| 1.0% | 190.81 (±14.04) |
| 2.0% | 498.62 (±49.50) |
| 5.0% | 1354.30 (±79.52) |

Clotrimazole solubility increased with increasing surfactant concentration. The relationship between drug solubility and PEG-20-oleyl ether concentration was found to be linear ($R^2$=0.9995). Thus, clotrimazole solubility was highest in the 5% surfactant solution. The solubility of clotrimazole in a 0.5% PEG-20-oleyl ether solution was 75.16 μg/mL. This was about 75-fold higher than the expected clotrimazole concentration of 1 μg/mL. Thus, the use of a 0.5% PEG-20-oleyl ether solution as the receptor phase would adequately ensure that sink conditions would be maintained throughout the experiment. Also, the lowest possible surfactant concentration was desirable so as to maintain as much physiological relevance as possible.

EXAMPLE 8

Antifungal Permeation Studies

Infinite Dose Studies. Each antifungal gel formulation was studied using 3 replicates. Excised, human fingernails (thumbnails and other fingernails), which had been standardized as described above, were used. Prior to the start of the study, baseline water permeation parameters were established for all nails as described above. The nails were assigned to different treatment groups, comprising 3 nails each, such that the mean, normalized water flux (J*) for each group was approximately equal. Permeation studies were conducted as described for enhancer screening studies.

Finite Dose Studies. The control gel and best test formulation, containing 10% MPG and 20% urea, were also studied using finite dosing to mimic the most convenient method of consumer application. The procedure was the same as that described for enhancer screening studies, however, the volume of each application was smaller. In the finite dose studies, the cells were dosed with 5 μL of the donor gels, the gels were spread evenly on the nail surface with a thin, plastic rod, and the diffusion cells were left uncovered. The exact amount of clotrimazole applied was calculated by subtracting the amount adhering to the rod from the total amount present in 5 μL volume. The rest of the procedure was as described above.

EXAMPLE 9

Analysis of Samples

Each of the samples (receptor solution and extractions) obtained during the permeation study was mixed with 10 mL of Scintiverse I (scintillation cocktail) and analyzed by Liquid Scintillation Counting (LSC, Beckman model LS 5000T, Beckman Instruments, Somerset, N.J.). Each sample was counted for at least 5 minutes and the counts in disintegrations per minute (dpm) were converted to amount of active, using the conversion factor 1 $\mu$Ci =2.2×10$^6$ dpm and the specific activity of $^3$H$_2$O or [$^3$H]-Clotrimazole.

EXAMPLE 10

Data Analysis of Enhancer Screen

The flux (J, mg cm$^{-2}$h$^{-1}$) was computed from the slope of the steady-state portion of the plot of cumulative amount of water permeated per unit area as a function of time. The normalized flux (J*, mg cm$^{-1}$h$^{-1}$) was calculated by multiplying the raw parameter by nail thickness. The normalized flux values (J*) from test formulations with enhancers were compared with the J* value of the appropriate control formulation having the same vehicle composition, but no enhancer using a t-test at the 0.05 level of significance. For effective enhancers, a statistically significant increase in normalized water flux was expected relative to the control.

A relative enhancement factor for water, $EF_{water}$, defined by Equation 1, was computed for each enhancer.

$$EF_{water} = \frac{J * \text{from test formulation (with enhancer)}}{J * \text{from control formulation (without enhancer}} \quad (1)$$

where J*=normalized flux of water (mg cm$^{-1}$h$^{-1}$).

The enhancers that resulted in the highest $EF_{water}$ values were considered to be the most effective.

EXAMPLE 11

Data Analysis of Antifungal Permeation Studies

The flux (J, $\mu$g cm$^{-2}$day$^{-1}$) was determined from the steady-state portion of the plot of cumulative amount of clotrimazole permeated per unit area as a function of time. The permeability coefficient (P, cm day$^{-1}$) was calculated by dividing the flux by the donor concentration of clotrimazole. The lag time ($t_{lag}$, days) was calculated from the x-intercept of the steady-state region of the permeation profile. The diffusion coefficient (D, cm$^2$day$^{-1}$) was computed from Equation 2.

$$t_L = \frac{h^2}{6D} \quad (2)$$

The normalized clotrimazole flux (J*, $\mu$g cm$^{-1}$day$^{-1}$) and normalized permeability coefficient (p*, cm$^2$day$^{-1}$) were calculated by multiplying the raw parameter by nail thickness, as shown in Equation 3 and Equation 4, respectively:

$$J^* = J \times h \quad (3)$$

where J*=normalized flux (mg cm$^{-1}$h$^{-1}$) and h=nail thickness (cm), and;

$$P^* = P \times h \quad (4)$$

where P*=normalized permeability coefficient (cm $^2$h$^{-1}$) The normalized flux values (J*) from the antifungal test formulations with enhancers were compared with the J* value of the control formulation having the same vehicle composition but no enhancer, using a t-test at the 0.05 level of significance.

A relative enhancement factor for clotrimazole, $EF_{clotrimazole}$, defined by Equation 5, was computed for each enhancer.

$$EF_{clotrimazole} = \frac{J * \text{from antifungal test formulation (with enhancer)}}{J * \text{from antifungal control formulation (without enhancer)}} \quad (5)$$

where J*=normalized flux of clotrimazole ($\mu$g cm$^{-1}$day$^{-1}$).

The EF value obtained for clotrimazole with a given enhancer was compared with the corresponding value obtained from screening studies with water. This comparison elucidated the degree to which a given enhancer increased the permeation of lipophilic vs hydrophilic molecules.

The amount of drug permeating into the nail was calculated from the sum of all extractions except the first extraction which was thought to contribute to drug at the nail surface. The amount of drug in the nail, expressed in $\mu$g/g, was compared for formulations with enhancers vs. the control using a t-test at the 0.05 level of significance.

EXAMPLE 12

Test for Barrier Integrity of Nails

Water permeation parameters were obtained after treatment with enhancers and antifungal agents and washout, and were compared with baseline values that had been established before screening had commenced. For the enhancer studies, the ratio of J* posttreatment to J* of the untreated nail was a measure of the barrier integrity. For the antifungal permeation studies, the relative increase in water flux due to a given enhancer, indicating a compromised barrier, was compared for lipophilic molecules (antifungals) and hydrophilic molecules (water) Thus, the degree to which the nail permeation barrier was compromised due to treatment with a given enhancer was compared for compounds of differing size and polarity.

What is claimed is:

1. A composition comprising sulfur-containing glycine residues and urea which increases the permeation of an active agent through nail tissue.

2. A method of treating a nail disease comprising topically applying the composition of claim 1 in an amount sufficient to increase the permeation of an active agent through nail tissue.

3. A method for enhancing the permeation of an active agent through nail tissue comprising administering an effective amount of the composition of claim 1.

* * * * *